United States Patent [19]
Kato

[11] Patent Number: 6,090,556
[45] Date of Patent: Jul. 18, 2000

[54] METHOD FOR QUANTITATIVELY DETERMINING THE EXPRESSION OF A GENE

[75] Inventor: Kikuya Kato, Osaka, Japan

[73] Assignee: Japan Science & Technology Corporation, Saitama, Japan

[21] Appl. No.: 09/056,052

[22] Filed: Apr. 6, 1998

[30] Foreign Application Priority Data

Apr. 7, 1997 [JP] Japan ................................... 9-088495

[51] Int. Cl.[7] .............................. C12Q 1/68; C12P 19/34; C07H 21/02; C07H 21/04
[52] U.S. Cl. ........................... 435/6; 435/91.1; 435/91.2; 435/91.21; 536/23.1; 536/23.2; 536/23.5; 536/24.3; 536/24.31; 536/24.32; 536/24.33
[58] Field of Search ............................... 435/6, 91.1, 91.2, 435/91.21; 536/23.1, 23.2, 23.5, 24.3, 24.31, 24.32, 24.33

[56] References Cited

U.S. PATENT DOCUMENTS 5,707,807  1/1998  Kato ............................................ 435/6
5,814,445  9/1998  Belyavsky et al. ......................... 435/6

FOREIGN PATENT DOCUMENTS

0534858 A1  3/1993  European Pat. Off. .
WO 94/23023 A1  10/1994  WIPO .
WO 97/05286 A1  2/1997  WIPO .

OTHER PUBLICATIONS

Kato, K., Adaptor–tagged comptetitive PCR: a novel method for measuring relative gene expression:, Nucleic Acid Research, 25:4694–4696 No. 2 (Nov. 1997).
Kato NAR vol. 24, No. 2 pp. 394–5, 1996.
Kato NAR vol. 23, No. 18 pp. 3685–3690, 1995.

Primary Examiner—Kenneth R. Horlick
Assistant Examiner—Jeffrey Siew
Attorney, Agent, or Firm—Fish & Richardson, P.C.

[57] ABSTRACT

The present invention relates to a method for quantitatively determining the expression of a gene, comprising providing at least two types of samples each containing a cDNA coding for the gene, adding a different adaptor to each of the cDNAs contained in the samples, mixing equal amounts of the samples each containing the adaptor-tagged cDNA, amplifying the resultant cDNAs and calculating an amount ratio between the amplified products.

3 Claims, 4 Drawing Sheets

FIG. 4
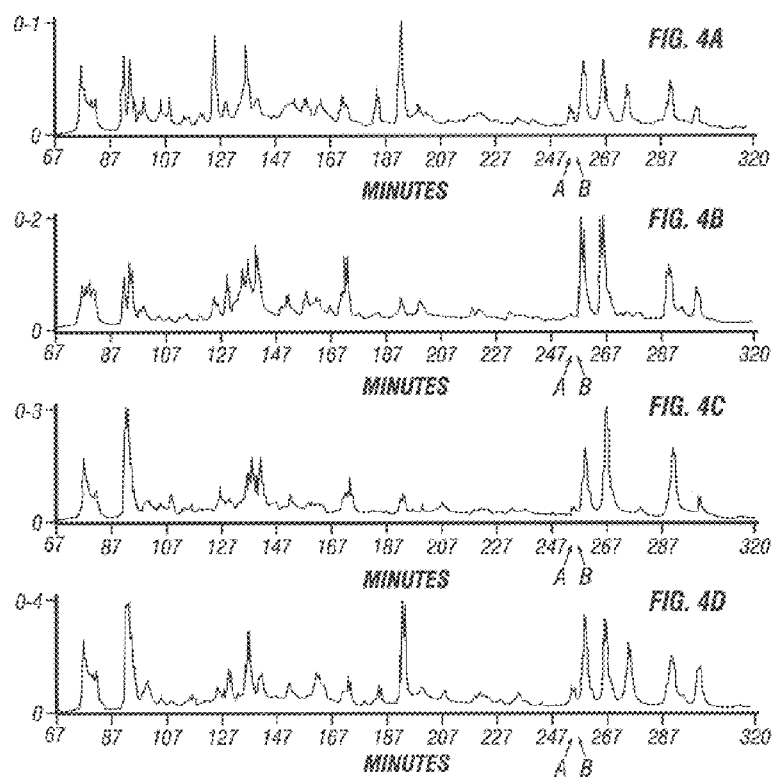

METHOD FOR QUANTITATIVELY DETERMINING THE EXPRESSION OF A GENE

BACKGROUND OF THE INVENTION

1. Field of the Invention

The present invention relates to a method for quantitatively determining the expression of a gene.

2. Description of the Prior Art

In order to determine the level of a gene expression, generally, Northern hybridization is carried out. For the routine determination at the laboratory level, the presence of 5 pg (picograms) of RNA is sufficient for detection. However, in cases where the amount of expression of a target gene is extremely small, 0.3–3 μg of mRNA is required for detection. Thus, it is difficult to apply Northern hybridization to cases where samples of limited amounts are only available (e.g., clinical samples).

Polymerase chain reaction (PCR) is a technique by which DNA or RNA can be detected most sensitively compared to other techniques. However, quantitative determination of a gene expression by PCR involves a control experiment in which a calibration curve is prepared using, as the so-called "internal control", a DNA fragment having an amplification efficiency similar to that of a target molecule. Thus, operations are complicated. Furthermore, in order to perform a quantitative PCR, it is necessary to prepare a calibration curve for each of the target genes to be quantitatively determined. Thus, a study of genes or a genetic diagnosis with this method requires much time and labor.

OBJECTS AND SUMMARY OF THE INVENTION

It is an object of the present invention to provide a method for quantitatively determining the expression of a gene.

As a result of intensive and extensive researches toward the solution of the problems described above, the present inventor has found that a gene expression can be quantitatively determined easily by providing at least two types of samples each containing a cDNA coding for the target gene, adding a different adaptor to each of the cDNAs contained in the samples and amplifying the resultant adaptor-tagged cDNAs in one reaction system. Thus, the present invention has been achieved.

The present invention relates to a method for quantitatively determining the expression of a gene, comprising providing at least two types of samples each containing a cDNA coding for the gene, adding a different adaptor to each of the cDNAs contained in the samples, mixing equal amounts of the samples each containing the adaptor-tagged cDNA, amplifying the resultant cDNAs and calculating an amount ratio between the amplified products. As the adaptors, those which comprise nucleotides having different lengths, nucleotides each having at least one restriction site, or nucleotides having different sequences may be used, for example.

BRIEF DESCRIPTION OF THE DRAWINGS

FIG. 3(*b*) presents the results of analysis of PCR products (amplified cDNA fragments shown as (b) in Table 1) using a sequencer.

FIG. 3(*c*) presents the results of analysis of PCR products (amplified cDNA fragments shown as (c) in Table 1) using a sequencer.

FIG. 3(*d*) presents the results of analysis of PCR products (amplified cDNA fragments shown as (d) in Table 1) using a sequencer.

FIG. 4 presents the results of analysis of PCR products (amplified cDNA fragments) using a sequencer.

DETAILED DESCRIPTION OF THE INVENTION

Hereinbelow, the present invention will be described in detail.

The present invention relates to a method for quantitatively determining an identical gene contained in plurality of samples by amplifying the gene in one reaction system comprising the samples. Briefly, the method of the invention is characterized by providing at least two types of samples each containing a cDNA coding for a target gene, adding a different adaptor sequence to each of the cDNAs contained in the samples, mixing equal amounts of the samples each containing the adaptor sequence-tagged cDNA, amplifying the resultant cDNAs and calculating an amount ratio between the amplified cDNAs. This method is called an adaptor-tagged competitive PCR (ATAC-PCR).

Hereinbelow, each step of this method will be described.

(1) Preparation of cDNA

Figure 1:
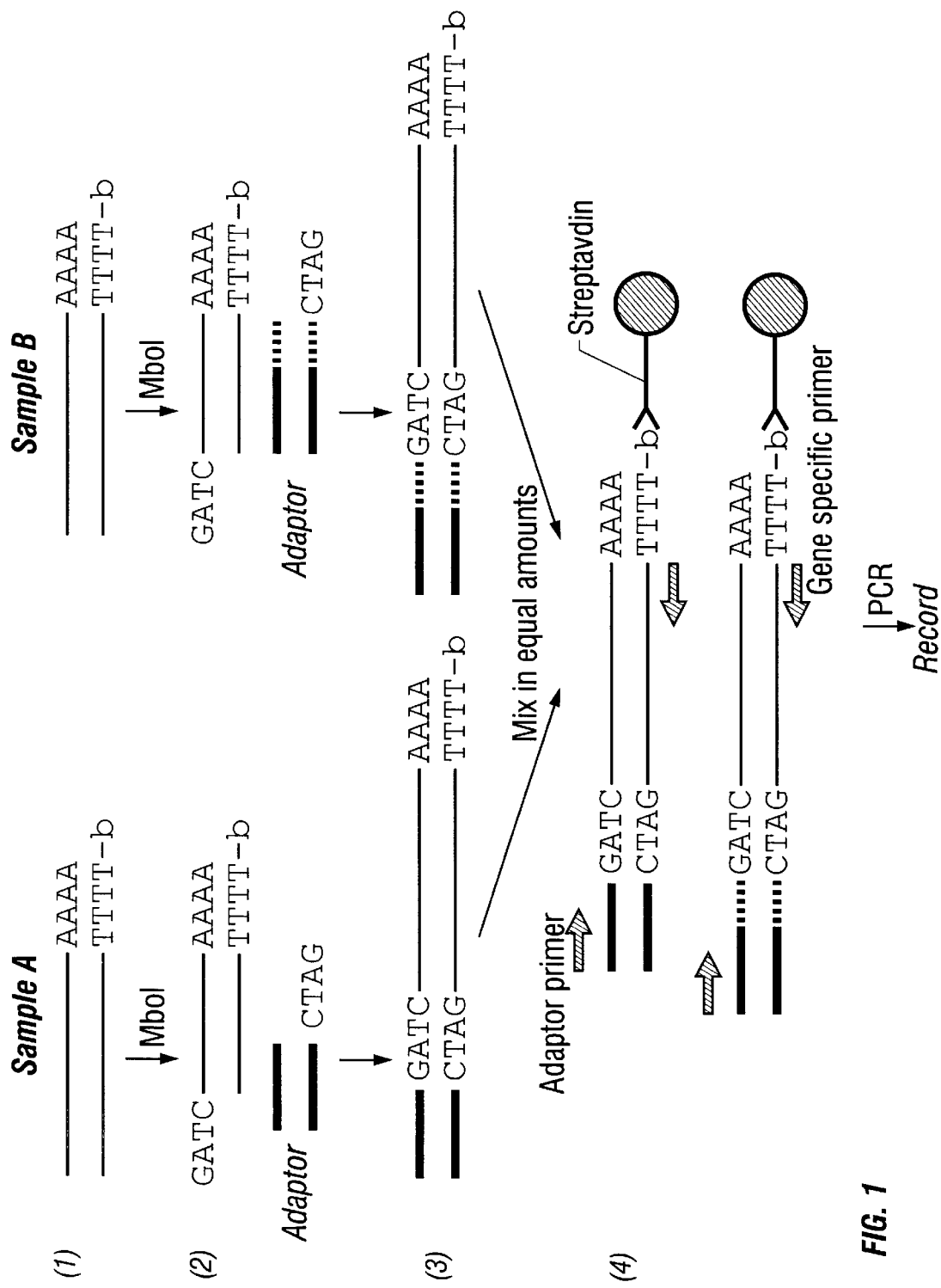
FIG. 1 is a schematic illustration of the method of the invention for quantitatively determining a gene expression.

As shown in FIG. 1, at least two types of samples each containing a cDNA to be determined are prepared. For the purpose of explanation, two types of samples each containing an identical cDNA are taken as an example.

One of the samples containing a cDNA is designated Sample A, and the other is designated Sample B. Preparation of the cDNA in Sample A and Sample B can be performed by any of the conventional techniques. For example, a technique of preparing poly(A)$^+$ RNA from cells of various organs and converting the RNA into cDNA with a reverse transcriptase (Gubler, U. and Hoffman, B. J., Gene, 25, 263–269 (1983); Okayama, H. and Berg, P., Mol. Cell. Biol., 18, 5294 (1982)) may be used.

In the present invention, Sample A and Sample B each containing a cDNA which is the target of quantitative determination may be derived from different tissues or cells, or may be derived from an identical tissue or cell. For example, Sample A may be a liver cell extract and Sample B may be a kidney cell extract. As the type of a cDNA to be quantitatively determined, those cDNAs derived from various organ RNAs including, but not limited to, a cDNA coding for a liver-derived apolipoprotein and a cDNA coding for a kidney-derived apolipoprotein may be given. The amount of a target cDNA in Sample A or Sample B may be known. Alternatively, the amount of a target cDNA may be unknown in both samples. When the amount of a target cDNA is known in one sample, then the absolute amount of the cDNA in the other sample can be determined. When the amount of a target cDNA is unknown in both samples, relative difference between the cDNA contents in Sample A and Sample B can be determined.

(2) Addition of Adaptors

Subsequently, the cDNAs in Sample A and Sample B are digested with a specific restriction enzyme (e.g., MboI, NlaIII, HpaII or TaqI). Then, a different adaptor is added to each of the cut sites [see FIG. 1, (1) and (2)]. An adaptor means an oligonucleotide which is designed so that a cDNA can be discriminated when amplified. An adaptor is designed as a double-stranded oligonucleotide so that it can be ligated to the cut site of a cDNA. The adaptors for use in the present invention may be designed so that one to be added to a cDNA in Sample A is different from one to be added to a cDNA in Sample B in length. Alternatively, they may be designed so that at least one restriction site is contained in each of the adaptors. Alternatively, they may be designed so that one to be added to a cDNA in Sample A is different from one to be added to a cDNA in Sample B in nucleotide sequence.

These adaptors are prepared as described below, for example. They can be obtained by chemical synthesis and they may be labelled with a fluorescent label or a radioisotope.

(i) Cases in Which Adaptors Having Different Lengths are Used

A common sequence for both adaptors (the bold line "—" in the adaptors in FIG. 1) is created. Then, a sequence of 5–15 bases is added to one of the adaptors so that they can be discriminated by length. At this time, the sequence to be added is designed so that it is located between the cohesive end of the cDNA and the binding site of an adaptor primer to be used for the subsequent amplification (see FIG. 2; the dotted line "⋯" in the adaptor for Sample B).

In order to remove excessive adaptors mixed in the sample (i.e., to recover the adaptor-tagged sample alone), it is preferable to add to the cDNA in each sample a substance (e.g., an antigen, an enzyme, biotin) which reacts with a specific substance (an antibody, a substrate, streptavidin) (FIG. 1). FIG. 1 illustrates biotin ("-b")-added cDNAs. However, when the amount of the starting material (RNA) for the sample is large, the relative difference between the amount of the cDNA obtained by reverse transcription of the RNA and the amount of free adaptor is considered to be small. Thus, there is no need to remove excessive adaptor in such a case. Therefore, the substance for a specific reaction as described above may not be added.

(ii) Cases in Which Restriction Site-Introduced Adaptors are Used

The restriction sites to be introduced into adaptors are designed so that one adaptor contains at least one restriction site. Alternatively, the number of such sites may be determined considering the number of samples each containing a target cDNA. The restriction site may be a site for MluI, NotI, SalI, SfiI, XhoI or the like.

When cDNAs contained in two samples are to be quantitatively determined, either one or two restriction sites may be introduced into one adaptor. The restriction site(s) is(are) designed so that it(they) is(are) located between the binding site of an adaptor primer and the cohesive end of the cDNA.

When one restriction site is introduced, the adaptor sequences are designed so that the two adaptors have different recognition sites with each other. For example, a SaiII site is introduced into an adaptor to be added to the cDNA in Sample A, and a MluI site into an adaptor to be added to the cDNA in Sample B.

Figure 2:
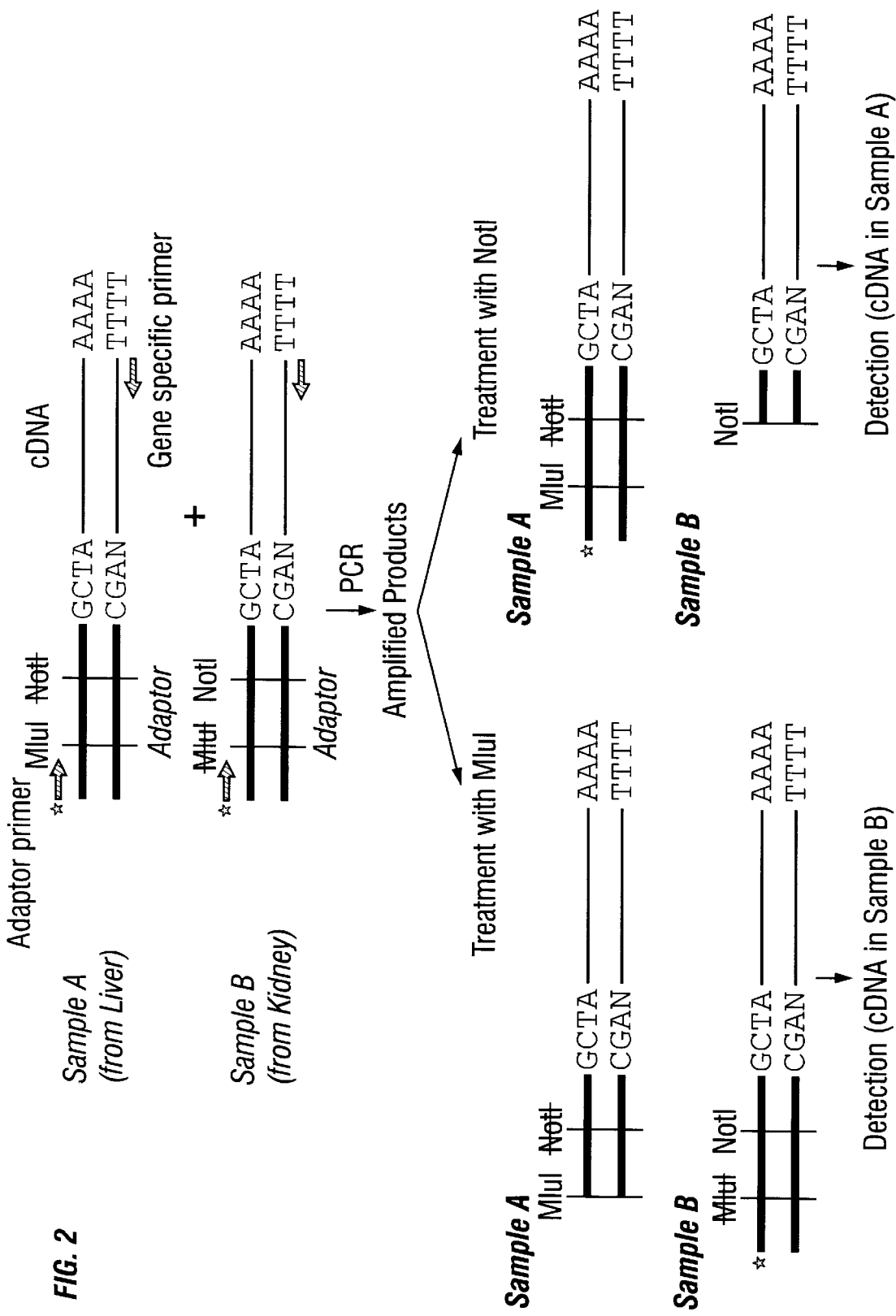
FIG. 2 is a schematic illustration of the method of the invention for quantitatively determining a gene expression.
Figure 3A:
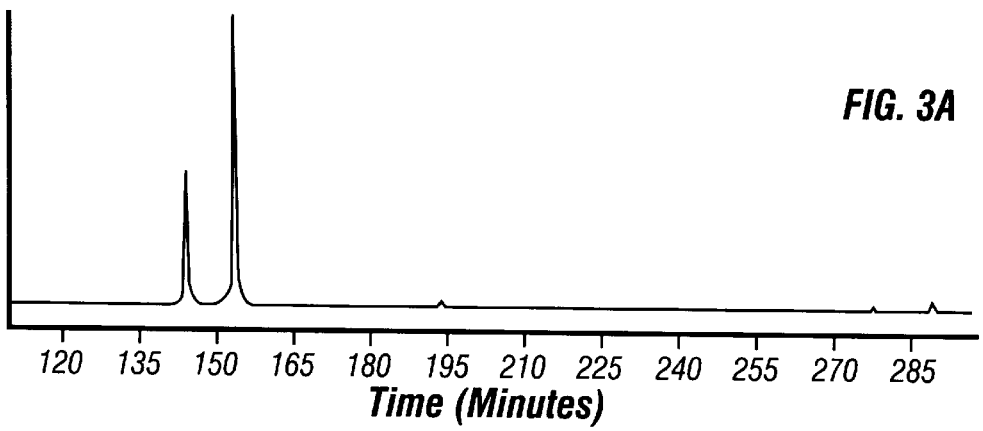
FIG. 3(*a*) presents the results of analysis of PCR products (amplified cDNA fragments shown as (a) in Table 1) using a sequencer.
Figure 3B:
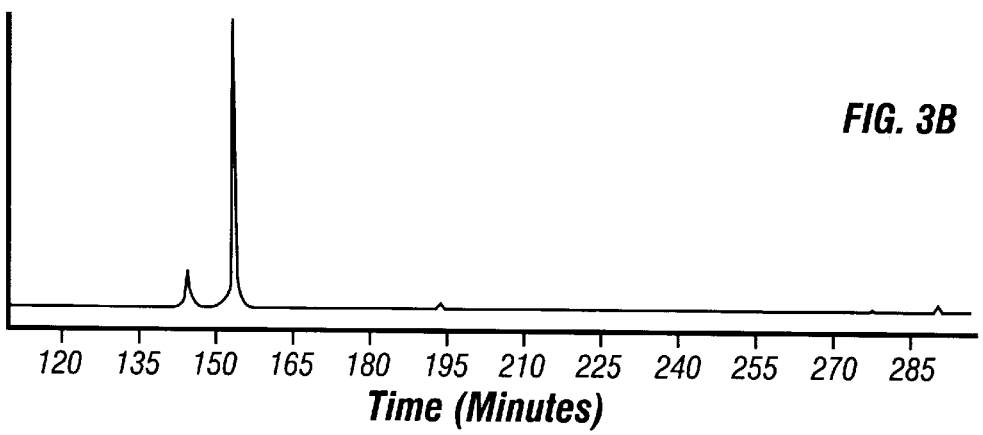
Figure 3C:
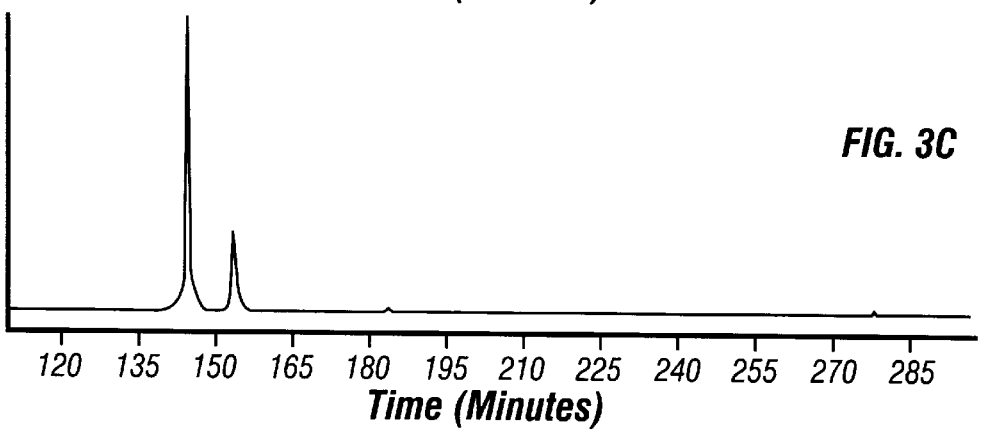
Figure 3D:
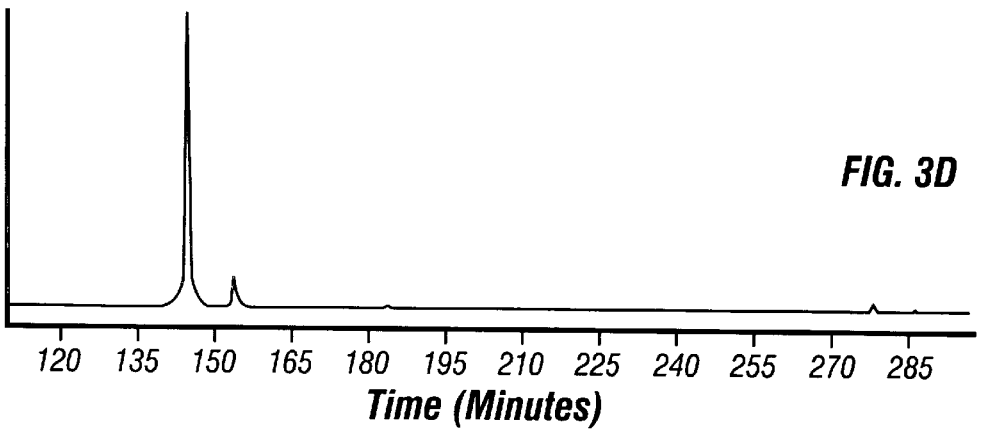

When two or more restriction sites are introduced, two different restriction sites are introduced into each adaptor to be added to the sample (FIG. 2). Furthermore, the adaptor is designed so that it is cut at only one of the two restriction sites when treated with a restriction enzyme. And yet, the adaptors are designed so that one restriction enzyme which cuts one adaptor tagged to one cDNA will not cut the other adaptor tagged to the other cDNA. For example, as shown in FIG. 2, when the cDNAs in Sample A and Sample B are quantitatively determined using adaptors each containing two restriction sites (e.g. for MluI and NotI), the adaptor tagged to the cDNA in Sample A is designed so that it is recognized by the restriction enzyme MuII alone. Specifically, a part of the NotI site of this adaptor is modified by substitution or the like so that this adaptor will not be recognized by the restriction enzyme NotI. (In FIG. 2, this is indicated by overwriting "NotI" with a bar.) At the same time, the adaptor tagged to the cDNA in Sample B is designed so that it is recognized the restriction enzyme NotI alone. In order for this adaptor not to be recognized by the restriction enzyme MluI, a part of its MluI site is modified by substitution or the like. (In FIG. 2, this is indicated by overwriting "MluI" with a bar.)

Preferably, biotin or the like is added to the cDNA so that the adaptor-tagged sample alone can be recovered.

(iii) Cases in Which Adaptors Having Different Nucleotide Sequences are Used

In the present invention, adaptors which are different from each other in nucleotide sequence may be discretionally designed, synthesized and used. When such adaptors are used, the target cDNA can be detected by preparing oligonucleotides which are complementary to those adaptors and thus hybridizable thereto, and labelling them.

For example, an adaptor to be added to a cDNA in Sample A is designated adaptor X and an adaptor to be added to a cDNA in Sample B is designated adaptor Y. These adaptors are designed so that the sequence of adaptor X is different from the sequence of adaptor Y except the region to which an adaptor primer is added, and so that a nucleotide hybridizing to adaptor X cannot hybridize to at least adaptor Y. The nucleotide sequences of adaptor X and adaptor Y can be designed discretionally and chemically synthesized. The lengths of the nucleotide sequences of these adaptors may be the same or different, ranging from 15 to 50 bases, preferably from 25 to 30 bases.

In these adaptors, the region to which an adaptor primer for subsequent amplification is to be added is common in sequence. Thus, the oligonucleotide to be hybridized to the adaptor should be designed and prepared so that it does not hybridize to the above-described region to which an adaptor primer is to be added. Accordingly, as long as this condition is satisfied, the region in the adaptor to which the oligonucleotide is hybridized is not particularly limited.

(3) Amplification of the cDNAs

Equal amounts of Sample A and Sample B each containing the adaptor-tagged cDNA are mixed. Then, amplification is carried out using the cDNAs in these samples as templates (FIGS. 1 and 2 ). This amplification is performed, for example, by polymerase chain reaction (PCR).

As primers, an adaptor primer and a gene specific primer are used. An adaptor primer is a primer which can hybridize to the adaptors designed as described above. A gene specific primer is a primer which can hybridize to at least a part of the cDNA to be quantitatively determined. Each of these Ma primers has a length of 20–25 bases and can be obtained, for W example, by chemical synthesis.

The number of PCR cycles and temperature conditions, etc. may be decided appropriately.

Each of the cDNA fragments is amplified maintaining its amount ratio. Since each fragment can be discriminated by the adaptor as to whether it is derived from liver mRNA or kidney mRNA, an absolute or relative amount of expression of the cDNA can be determined from an amount ratio between the final products by the detection and quantitative determination described below.

(4) Detection and Quantitative Determination of the Amplified Products

After a PCR is performed on the mixed sample, the amplified products are detected with an autosequencer (from Pharmacia, etc.) or an image scanner (from Molecular Dynamics) when a fluorescent label was used, or with a densitometer or the like when a radioisotope was used.

(i) Cases in Which Adaptors Having Different Lengths are Used

Based on the data obtained by the detection, the amount ratio between the cDNAs in two samples ($m_1/m_2$) is calculated using the following formulas. The datum (observed value) obtained by the detection (designated "$a_1$") can be expressed by formula I below:

$$a_1 = m_1/m_2((1+e_1)^n/(1+e_2)^n) \quad (I)$$

wherein $m_1$ represents the amount of the cDNA in Sample A; $m_2$ represents the amount of the cDNA in Sample B; $e_1$ and $e_2$ individually represents a constant ranging from 0 to 1 and the amplification efficiency of each adaptor-tagged cDNA for a single cycle; and n is the number of cycles.

Preferably, the adaptors added to the cDNAs in the two samples are exchanged with each other, and then similar amplification and determination are performed to determine an amount ratio ($m_1/m_2$).

The observed value obtained in the second test using the exchanged adaptors is designated "$b_1$", which can be expressed by formula II below:

$$b_1 = m_1/m_2((1+e_2)^n/(1+e_1)^n) \quad (II)$$

From formulas I and II, the geometric average of the amount ratio $m_1/m_2$ can be expressed by formula III below:

$$m_1/m_2 = (a_1 b_1)^{1/2} \quad (III)$$

(ii) Cases in Which Restriction Site-Introduced Adaptors are Used

On the other hand, when adaptors are designed so that each of them contains restriction sites (e.g., two restriction sites for MluI and NotI), samples each containing the adaptor-tagged cDNA are mixed in equal amounts and subjected to a PCR. Thereafter, the cDNA in Sample A is digested with MluI and the cDNA in Sample B is digested with NotI, to thereby detect the amplified cDNAs discriminating the adaptors added thereto. Since the cut site is different in these adaptors, the amplified fragments will have different lengths. Thus, an amount ratio of the cDNA in Sample A to the cDNA in Sample B can be obtained.

Briefly, when the adaptor primer used in the PCR has been labelled with a fluorescent dye, a radioisotope or the like, the resultant amplified products are labelled with the fluorescent dye or the radioisotope (FIG. 2, mark "☆") Thus, those fragments digested with a restriction enzyme are not detected since their labelled site has been removed. As a result, only those fragment which were not digested with the restriction enzyme are detected. By comparing (a) the fragment which appears as an electrophoresis band or an electropherogram from an autosequencer-when treated with one restriction enzyme with (b) the fragment which appears as a band or an electropherogram when treated with the other restriction enzyme, an amount ratio between both cDNAs can be determined. For example, when a PCR was performed using adaptors each containing a MluI site and a NotI site and then the reaction solution was electrophoresed, the band which appears when the amplified products were treated with MluI is the cDNA derived from Sample B, whereas the band which appears when the amplified products were treated with MluI is the cDNA derived from Sample A (FIG. 2). Then, both bands can be converted into numerical values with a densitometer or the like, followed by calculations as described in (i) above. Thus, an amount ratio between the cDNAs can be obtained.

Even when the number of restriction sites introduced into each of the adaptors is one, the amplified cDNAs can be detected in a similar manner provided that each adaptor contains a different restriction site from each other. In this case, the amplified products are divided into two portions, each of which is treated with one of the relevant restriction enzymes. As a result, fragments with different lengths can be obtained. For example, in FIG. 2, an adaptor having a SalI site alone is added to the cDNA in Sample A (derived from liver) and an adaptor having a MluI site alone is added to the cDNA in Sample B (derived from kidney) instead of the adaptors used in this Figure. These samples are mixed in equal amounts and subjected to a PCR. Then, the reaction solution is divided into two portions. One is treated with SalI and the other is treated MluI. As a result, a MluI site-containing fragment (i.e., the cDNA derived from kidney) is detected in the SalI-treated portion, and a SalI site-containing fragment (i.e., the cDNA derived from liver) is detected in the MluI-treated portion. From these results, an amount ratio of expression between the cDNAs in both samples can be determined. By repeating the same procedures after exchanging the adaptors, the liver-derived cDNA is detected by SalI treatment and the kidney-derived cDNA by MluI treatment. Then, an amount ratio of expression between the cDNAs is determined similarly. Thereafter, a geometric average of this ratio and the previously obtained ratio can be calculated.

(iii) Cases in Which Adaptors Having Different Nucleotide Sequences are Used

First, oligonucleotides are synthesized which are complementary to the oligonucleotide sequences of the individual adaptors prepared as described above, respectively, and thus specifically hybridizable thereto. As explained above, each of these oligonucleotides is designed and synthesized so that it can hybridize to one adaptor but cannot hybridize to the other adaptor. These oligonucleotides have only to hybridize to one of the two strands of the adaptors.

Subsequently, the oligonucleotide sequences thus prepared are labelled. As a labelling substance, a fluorescent dye or a radioisotope is used, for example.

After two samples are mixed in equal amounts and subjected to a PCR, the labelled oligonucleotides described above are added to the amplified products to allow hybridization of the labelled oligonucleotides to the sequences of the adaptor regions (excluding the region to which the adaptor primer is added), respectively. Here, each of the amplified cDNAs having the adaptor sequence is formed as a double-stranded cDNA. Thus, the above hybridization is performed after the amplified products have been converted into single-stranded cDNAs. The denaturation from double-stranded cDNA to single-stranded cDNA may be carried out by, for example, a denaturing reaction in PCR (e.g., at 94° C. for 30 seconds). The hybridization may be carried out by, for example, an annealing reaction in PCR (e.g., at 55° C. for 1 minute).

It should be noted, however, that the adaptor strand to which the above oligonucleotide is to be hybridized must be fixed to a solid phase in order to remove the free, labelled-oligonucleotide after hybridization. For the fixation, a combination of biotin-streptavidin or the like is used. In this case, streptavidin is fixed to a solid phase, and biotin is bound to the adaptor strand to which the oligonucleotide is to be hybridized. By these procedures, a hybridized strand can be easily fixed.

Finally, the fluorescence intensity or concentration of the labelling substance is determined after the hybridization. Thus, an amount ratio between the cDNAs can be calculated in the same manner as described above.

(5) Application to the Molecular Indexing

The method of the invention is applicable to the quantitatively determination of cDNA fragments classified by the so-called molecular indexing.

The molecular indexing is a method of classifying expressed genes (cDNAs) by using specific 3 restriction enzymes (class IIS restriction enzymes, e.g., FokI, BsmAI and BamFI) and oligonucleotides to be ligated to the cut sites generated by the above restriction enzymes. According to the molecular indexing, expressed genes (cDNAs) are classified into 576 groups, and the individual fragments are separated from each other (Kikuya Kato, "Discriminatory Representation Technique for Expressed Genes", Bio Industry, 13 (6), pp.16–23, 1996; Japanese Unexamined Patent Publication No. 8-322598; and U.S. Pat. No. 5,707, 807).

In the present invention, at least two samples each containing a target cDNA fragment classified by the molecular indexing are mixed in equal amounts and amplified. Thereafter, an amount ratio between the cDNA fragments can be obtained. By introducing one or more restriction sites into the oligonucleotides used in the molecular indexing, the oligonucleotides can be used as adaptors in the present invention. Then, an amplification reaction similar to that described above can be performed to quantitatively determine the cDNA fragment.

The molecular indexing is a method in which a large number of fragments are amplified by PCR. The application of the method of the invention (i.e., adaptor-tagged competitive PCR (ATAC-PCR)) thereto is advantageous, because identification of those fragments exhibiting difference in expression becomes easy even if a non-specific reaction product appears in samples in common.

PREFERRED EMBODIMENTS OF THE INVENTION

The present invention will be described more specifically below with reference to the following Examples, which should not be construed as limiting the technical scope of the invention.

EXAMPLE 1

Adaptor-Tagged Competitive PCR

In this Example, an amount ratio between a cDNA coding for mouse liver-derived apolipoprotein and a cDNA coding for mouse kidney-derived apolipoprotein was determined using mouse liver tissues and mouse kidney tissues.

(1) Synthesis of Single-Stranded cDNA

Mouse liver-derived total RNA and mouse kidney-derived total RNA were prepared separately from mouse frozen tissues (liver and kidney) by the guanidine isothiocyanate method. To 7 µl of distilled water containing 3 µg of the total RNA, a chemically synthesized biotinylated oligo $(dT)_{18}$ primer was added and heated at 70° C. for 2–3 minutes. Then, the resultant solution was placed in a reaction solution of the following composition and kept at 37° C. for 1 hour.

| Composition of the Reaction Solution | |
| --- | --- |
| 5x Reverse transcriptase buffer | 4 µl |
| 2 mM dNTP | 4 µl |
| 0.1M DTT | 2 µl |
| 10 pmol/µl 5'-biotinylated oligo$(dT)_{18}$ primer | 1.5 µl |
| RNase inhibitor (40 U/µl) | 0.5 µl |
| 200 U/µl M-MLV reverse transcriptase | 1 µl |

(2) Synthesis of Double-Stranded cDNA

To each of the mouse liver-derived and mouse kidney-derived single-stranded cDNAs obtained in (1) above, a reaction solution of the following composition was added and reacted at 16° C. for 1 hour and then at room temperature for 1 hour to synthesize double-stranded cDNA separately.

Composition of the Reaction Solution

| Composition of the Reaction Solution | |
| --- | --- |
| 10 mM $MgCl_2$ | 70.5 µl |
| 1M Tris-HCl (pH 7.5) | 10 µl |
| 1M $(NH_4)_2SO_4$ | 1.5 µl |
| RNase H (1U/µl) | 1.5 µl |
| E. coli DNA polymerase (10 U/µl) | 4.5 µl |

After completion of the reaction, 3 µl of 0.25 M EDTA (pH 7.5) and 2 µl of 5 M NaCl were added to the reaction solution, which was then subjected to phenol extraction and ethanol precipitation. The resultant cDNA was dissolved in 120 µl of distilled water.

(3) Digestion with a Restriction Enzyme

A reaction solution of the following composition was kept at 30° C. for 1 hour.

| | |
| --- | --- |
| 10x M buffer | 5 µl |
| cDNA sample obtained in (2) | 45 µl |
| Restriction enzyme MboI | 5 U |

After completion of the reaction, the reaction solution was heated at 75° C. for 10 minutes, diluted with 9 volumes of distilled water and then used in the adaptor addition reaction described below.

(4) Adaptor Addition Reaction

| | |
| --- | --- |
| 10x Ligation buffer | 1.5 µl |
| 10 pmol/µl Adaptor MA-1 or MA-4 | 3 µl |
| Mouse liver-derived and/or kidney-derived cDNA (see Table 1) | 10 µl |
| 350 U/µl T4 DNA ligase | 0.5 µl |

As samples, the mouse liver-derived cDNA and a mixture of the mouse liver-derived and mouse kidney-derived cDNAs were used. The combinations of samples and adaptors were as shown in Table 1 below.

TABLE 1

| | Sample A | Adaptor | Sample B | Adaptor |
|---|---|---|---|---|
| (a) | Mouse liver cDNA 10 µl | MA-4 | Mouse liver cDNA 3 µl + Mouse kidney cDNA 7 µl | MA-1 |
| (b) | Mouse liver cDNA 10 µl | MA-4 | Mouse liver cDNA 1 µl + Mouse kidney cDNA 9 µl | MA-1 |
| (c) | Mouse liver cDNA 10 µl | MA-1 | Mouse liver cDNA 3 µl + Mouse kidney cDNA 7 µl | MA-4 |
| (d) | Mouse liver cDNA 10 µl | MA-1 | Mouse liver cDNA 1 µl + Mouse kidney cDNA 9 µl | MA-4 |

As a gene specific primer, an apolipoprotein A-1 specific primer was used. As an adaptor primer, C1S (labelled with Cy5) was used. The sequences for individual primers are as follows:

Apolipoprotein A-1 specific primer:
   5'-TTATTGTAAGAAAGCCAATGCG-3' (SEQ ID NO: 1)

Adaptor primer C1S:
   5'-GTACATATTGTCGTTAGAACGC-3' (SEQ ID NO: 2)

The sequences for adaptors are as follows:
MA-1:
   5'-GATCCGCGTTCTAACGACAATATGTAC-3' (+ strand; SEQ ID NO: 3)
   3'-GCGCAAGATTGCTGTTATACATG-5' (− strand; SEQ ID NO: 4)

MA-4:
   5'-GATCGAGCACTCTTAGCGTTCTAACGACAA-TATGTAC-3' (+ strand; SEQ ID NO: 5)
   3'-CTCGTGAGAATCGCAAGATTGCTGTTATACA-TG-5' (− strand; SEQ ID NO: 6)

A reaction solution of the above-described composition was kept at 16° C. overnight.

(5) PCR

To each of the samples, 5 µl of 5 M NaCl and 3 µl of 10 mg/ml streptavidin-coated paramagnetic beads were added and left stationary for 20 minutes to allow the beads to adsorb the sample. Thereafter, two samples each containing a cDNA to be determined were mixed as indicated in Table 1. Then, the beads were washed with distilled water and divided into four equal portions, to each of which a reaction solution of the following composition was added.

| | |
|---|---|
| 10x Buffer for Stoffel fragment | 1 µl |
| 25 mM MgCl$_2$ | 1.5 µl |
| 2 mM dNTP | 1 µl |
| 10 pmol/µl Cy5-labelled C1S | 0.25 µl |
| 10 pmol/µl Apolipoprotein A-1 specific primer | 0.25 µl |
| Stoffel fragments | 1 unit |
| Distilled water to make 10 µl | |

For each reaction solution of the above-described composition, a PCR was performed. The PCR cycle was as follows: 30–35 cycles of denaturation at 94° C. for 30 seconds, annealing at 55° C. for 1 minute and extension at 72° C. 1 minute; then, final extension at 72° C. for 20 minutes.

After completion of the reaction, a solution of the following composition was added and kept at 37° C. for 1 hour.

| | |
|---|---|
| 10x M buffer (TaKaRa) | 0.5 µl |
| Distilled water | 4.5 µl |
| T4 DNA polymerase | 0.1 unit |

After thermal denaturation of the final product, 0.5 µl thereof was analyzed with Pharmacia ALF Express Sequencer.

The results are shown in FIG. 3. Using formulas I and II, the values of $a_1$ and $b_1$ for the sample combinations (a), (b), (c) and (d) were calculated from peak areas. As a result, values shown in Table 2 below were obtained.

TABLE 2

| | MA-1-added Fragments | MA-4-added Fragments | Amount Ratio |
|---|---|---|---|
| (a) | 2432.5 | 5535.5 | 0.439 |
| (b) | 542.27 | 4615.5 | 0.117 |
| (c) | 5246.2 | 1459.5 | 0.278 |
| (d) | 6146.2 | 525.02 | 0.085 |

In Table 2, the results of (a) and (c) were obtained by exchanging the adaptor primers from each other. Also, the results of (b) and (d) were obtained similarly. The indications (a), (b), (c) and (d) in Table 2 correspond to (A), (B), (C) and (D) in FIG. 3, respectively.

From these results, geometric average was calculated based on formula III. The results are as described below.
  i) The ratio (liver cDNA 3 µl + kidney cDNA 7 µl)/(liver cDNA 10 µl ): [(a) and (c) in Table 2]
    $m_1/m_2 = 0.35$ (expected value: 0.3)
  ii) The ratio (liver cDNA 1 µl + kidney cDNA 9 µl)/(liver cDNA 10 µl ): [(b) and (d) in Table 2]
    $m_1/m_2 = 0.10$ (expected value: 0.1)

Since apolipoproteins are expressed only in the liver, the ratio of each peak is expected to correspond to the ratio of liver cDNA. As seen from the above results, almost expected values could be obtained.

EXAMPLE 2

Application to Molecular Indexing (1) Synthesis of cDNA

The synthesis of cDNA was performed in the same manner as in Example 1 using mouse liver-derived and mouse kidney-derived total RNAs. However, instead of the usual oligo-dT primer, the following primers (called "double-anchored oligo-dT primer(s)") were used in a mixture combined in equal amounts. As an amount of this mixed primer, 1.5 ml of 10 pmol/µl mixed primers was used.

| | |
|---|---|
| 5'-GGATCCTTTTTTTTTTTTTTTA-3' | (SEQ ID NO: 7) |
| 5'-CAGCTGTTTTTTTTTTTTTTTA-3' | (SEQ ID NO: 8) |
| 5'-CTCGAGTTTTTTTTTTTTTTTA-3' | (SEQ ID NO: 9) |

(2) Digestion with the Class IIS Restriction Enzyme FokI

A reaction solution of the following composition was kept at 37° C. for 50 minutes to 1 hour.

| | |
|---|---|
| 10x M buffer (TaKaRa) | 5 µl |
| 0.1% BSA | 5 µl |

| | |
|---|---|
| cDNA sample | 40 μl |
| Restriction enzyme FokI (10 U/μl) | 0.5 μl |

(3) Adaptor Addition Reaction

As adaptors, the following two adaptors each containing one restriction enzyme recognition site were used.

i) Nxyz-C1GMR

This biotinylated adaptor has at its cohesive end a base sequence Nxyz [wherein N represents A, G, C or T (a mixture of 4 bases); and xyz represents one of the possible 64 sequences that 3 bases can take] and has a recognition site for the restriction enzyme SalI within its adaptor sequence. The sequences of this adaptor are as follows:

5'-biotin-GTACATATTGTCGTTAGAACGCACTCGTCGAC-GCG-3' (+ strand, SEQ ID NO: 10)
5'-NxyzCGCGTCGACGAGTGCGTTCTAACGACAA-TATGTAC-3' (− strand, SEQ ID NO: 11)

ii) Nxyz-C1GSR

This biotinylated adaptor has at its cohesive end a base sequence Nxyz [wherein N represents A, G, C or T (a mixture of 4 bases); and xyz represents one of the possible 64 sequences that 3 bases can take] and has a recognition site for the restriction enzyme MluI within its adaptor sequence. The sequences of this adaptor are as follows:

5'-biotin-GTACATATTGTCGTTAGAACGCACGCGTCTAC-GCG-3' (+ strand, SEQ ID NO: 12)
5'-NxyzCGCGTAGACGCGTGCGTTCTAACGACAA-TATGTAC-3' (− strand, SEQ ID NO: 13)

Using the above adaptors, a ligation reaction was performed in a reaction solution of the following composition.

| | |
|---|---|
| 10x E. coli ligase buffer | 1 μl |
| 100 mM (NH$_4$)$_2$SO$_4$ | 1 μl |
| 0.5 mM NAD | 1 μl |
| 10 pmol/μl Adaptor solution | 1 μl |
| cDNA sample described above | 1 μl |
| E. coli DNA ligase | 6 units |

Distilled water was added to make the solution 10μl. The resultant solution was kept at 16° C. overnight.

After completion of the ligation reaction, 40 μl of distilled water and 5 μl of 10× T buffer (NEB buffer 4) were added to the sample, to which 0.3 unit of the restriction enzyme BsmFI was added further. The resultant sample was kept at 65° C. for 50 minutes.

(4) Recovery of the Adaptors with Paramagnetic Beads

Microtubes into which beads were to be dispensed were coated with PBS 0.1% BSA. The microtubes were washed with 1× B&W buffer (10 mM Tris-HCl, pH 7.5, 1 M NaCl, 1 mM EDTA) twice. Streptavidin-coated paramagnetic beads were washed with 1× B&W buffer (10 mM Tris-HCl, pH 7.5, 1 M NaCl, 1 mM EDTA) twice and suspended in an equal volume of 1× B&W buffer. Additionally, 0.1 M NaOH was prepared by diluting 5 N NaOH. These operations were carried out immediately before the adaptor recovery.

To the sample, 15 μl of 5 M NaCl and 5 μl of 10 mg/ml paramagnetic beads were added. The resultant sample was left stationary for 20 minutes under occasional agitation.

Two samples to be compared were mixed and washed with 50 μl of 0.1 M NaOH once. Then, the sample mixture was washed with 50 μl of 1× B&W Buffer once and with 50 μl of distilled water twice.

(5) Primary PCR

The beads on which cDNA was adsorbed were divided into 3 equal portions. Then, a PCR was performed in a reaction solution of the following composition.

| Enzyme Reaction Solution | |
|---|---|
| 10x PCR buffer for Stoffel fragment | 1 μl |
| 2 mM dNTP | 1 μl |
| 25 mM MgCl$_2$ | 1.2 μl |
| Distilled water | 3.7 μl |
| 10 U/μl Stoffel fragment | 0.13 μl |
| 10 pmol/μl unlabelled C1S | 1 μl |
| 10 pmol/μl double-anchored primer (A, C or G) | 2 μl |

The PCR was performed 20 cycles, one cycle consisting of denaturation at 94° C. for 1 minute, annealing at 55° C. for 1 minute and extension at 72° C. 1 minute.

(6) Digestion with Restriction Enzymes

After completion of the primary PCR, two 5 μl samples were taken from the reaction solution. To one sample, 5 μl of 5× high buffer containing 1 unit of the restriction enzyme MulI was added. To the other sample, 5 μl of 5× high buffer containing 1 unit of the restriction enzyme SalI was added. The samples were kept at 37° C. for 1 hour.

(7) Secondary PCR

A PCR was performed in a reaction solution of the following composition.

| Enzyme Reaction Solution | |
|---|---|
| 10x PCR buffer for Stoffel fragment | 1 μl |
| 2 mM dNTP | 1 μl |
| 25 mM MgCl$_2$ | 1.2 μl |
| Distilled water | 3.7 μl |
| 10 U/μl Stoffel fragment | 0.13 μl |
| 10 pmol/μl Texas Red-labelled C1S | 1 μl |
| 10 pmol/μl double-anchored primer (A, C or G) | 2 μl |
| cDNA sample mixture treated with restriction enzymes in (6) above | 1 μl |

The PCR was performed 20 cycles, one cycle consisting of denaturation at 94° C. for 1 minute, annealing at 55° C. for 1 minute and extension at 72° C. 1 minute. After completion of the reaction, a T4DPase mix of the following composition was added to the reaction solution, which was then kept at 37° C. for 1 hour.

| Composition of T4DPase Solution (per Sample) | |
|---|---|
| 10x M buffer | 0.5 μl |
| 2 mM dNTP | 0.5 μl |
| Distilled water | 4 μl |
| T4 DNA polymerase | 0.5 unit |

The resultant solution was heated at 72° C. for 10 minutes and then subjected to dialysis. 2 μl of the dialysate was thermally denatured and applied to a Hitachi automatic sequencer.

The results are shown in FIG. 4, which is a representation on fluorograms and FIGS. 4A–D is a representation on electropherograms. "A" in the Figure represents the fluorescence intensity of a target fragment of detection. "B" in the Figure represent the fluorescence intensity of a non-specifically expressed fragment appearing in both samples compared. In FIG. 4, "a" represents a sample in which Nxyz-C1GMR (xyz=CTC) and liver cDNA were ligated, and "b" represents a sample in which Nxyz-C1GSR (xyz=

CTC) and kidney cDNA were ligated. These samples were mixed together and subjected to a PCR using double anchored primer C. "a" was digested with the restriction enzyme MluI, and "b" with the restriction enzyme SalI. In FIG. 4, "c" represents a sample in which Nxyz-C1GMR (xyz=CTC) and kidney cDNA were ligated, and "d" represents a sample in which Nxyz-C1GSR (xyz=CTC) and liver cDNA were ligated. These samples were mixed together and subjected to a PCR using double anchored primer C. "c" was digested with the restriction enzyme MluI, and "d" with the restriction enzyme SalI.

The fluorescence intensity of each of the amplified a fragments is shown in Table 3 below. In this Table, the fluorescence intensity of the target fragment was corrected with the fluorescence intensity of the non-specific fragment expressed in both samples to be compared.

TABLE 3

|   | Fluorescence Intensity A | Fluorescence Intensity B | Corrected Value (A/B) |
|---|---|---|---|
| a | 500 | 1896 | 0.264 |
| b | 127 | 1944 | 0.0653 |
| c | 88 | 1940 | 0.0454 |
| d | 467 | 2340 | 0.200 |

Since "a" and "d" represent liver-derived fragments, and "b" and "c" represent kidney-derived fragments, the ratio of the expression of a target fragment in liver to the expression thereof in kidney is expressed by a/b and by d/c. According to the corrected values, a/b is 4.04 and d/c is 4.41. Thus, the geometric average of those amount ratios is 4.21. Accordingly, the method of the invention could be successfully applied to molecular indexing to obtain an amount ratio between amplified products.

EFFECT OF THE INVENTION

According to the present invention, a method for quantitatively determining the expression of a gene is provided. The method of the present invention is especially useful for handling a large number of samples such as clinical samples, or quantitatively determining a large number of genes.

What is claimed is:

1. A method for quantitatively determining the expression of a gene, comprising providing at least two samples each containing a cDNA coding for the gene, adding a different adaptor to each of the cDNAs contained in the samples, mixing the samples together, each sample including the adaptor-added cDNA, amplifying the resultant cDNAs and calculating an amount ratio between the amplified products.

2. The method of claim 1, wherein said different adaptors comprise nucleotides different from each other in length or nucleotides having at least one different restriction site.

3. The method of claim 1, wherein said different adaptors comprise nucleotides different from each other in sequence.

* * * * *

SEQUENCE LISTING

<160> NUMBER OF SEQ ID NOS: 13

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic DNA

<400> SEQUENCE: 1
ttattgtaag aaagccaatg cg                                    22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic DNA

<400> SEQUENCE: 2
gtacatattg tcgttagaac gc                                    22

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic DNA

<400> SEQUENCE: 3
gatccgcgtt ctaacgacaa tatgtac                               27

<210> SEQ ID NO 4
<211> LENGTH: 23
<212> TYPE: DNA
<213> ORGANISM: Artificial Sequence

```
<220> FEATURE:
<223> OTHER INFORMATION: Description of Artificial Sequence: Synthetic DNA

<400> SEQUENCE: 4
gtacatattg tcgttagaac gcg                                              23

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: Synthetic DNA

<400> SEQUENCE: 5
gatcgagcac tcttagcgtt ctaacgacaa tatgtac                               37

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic DNA

<400> SEQUENCE: 6
gtacatattg tcgttagaac gctaagagtg ctc                                   33

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic DNA

<400> SEQUENCE: 7
ggatcctttt ttttttttt tta                                               23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic DNA

<400> SEQUENCE: 8
cagctgtttt ttttttttt tta                                               23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic DNA

<400> SEQUENCE: 9
ctcgagtttt ttttttttt tta                                               23

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic DNA

<400> SEQUENCE: 10
gtacatattg tcgttagaac gcactcgtcg acgcg                                 35
```

```
<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic DNA
<220> FEATURE:
<221> NAME/KEY: misc_feature
<222> LOCATION: (1)..(4)
<223> OTHER INFORMATION: 'n' can be any base A, T, C or G

<400> SEQUENCE: 11
nnnncgcgtc gacgagtgcg ttctaacgac aatatgtac                              39

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic DNA

<400> SEQUENCE: 12
gtacatattg tcgttagaac gcacgcgtct acgcg                                  35

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic DNA
<220> FEATURE:
<221> NAME/KEY: misc_feature
<222> LOCATION: (1)..(4)
<223> OTHER INFORMATION: 'n' can be any base A, T, G, or C

<400> SEQUENCE: 13
nnnncgcgta gacgcgtgcg ttctaacgac aatatgtac                              39
```